(12) United States Patent
Tonouchi et al.

(10) Patent No.: US 8,637,463 B2
(45) Date of Patent: Jan. 28, 2014

(54) PEPTIDE INHIBITING ANGIOTENSIN CONVERTING ENZYME

(75) Inventors: Hidekazu Tonouchi, Odawara (JP);
Masayuki Suzuki, Odawara (JP);
Masayuki Uchida, Odawara (JP);
Munehiro Oda, Odawara (JP)

(73) Assignee: Meiji Dairies Corporation, Tokyo (JP)

( * ) Notice: Subject to any disclaimer, the term of this patent is extended or adjusted under 35 U.S.C. 154(b) by 817 days.

(21) Appl. No.: 10/581,304

(22) PCT Filed: Dec. 1, 2004

(86) PCT No.: PCT/JP2004/018235
§ 371 (c)(1),
(2), (4) Date: Nov. 2, 2006

(87) PCT Pub. No.: WO2005/061529
PCT Pub. Date: Jul. 7, 2005

(65) Prior Publication Data
US 2009/0163425 A1  Jun. 25, 2009

(30) Foreign Application Priority Data
Dec. 1, 2003  (JP) .............................. P. 2003-401405

(51) Int. Cl.
*A61K 38/06* (2006.01)
*A61K 38/07* (2006.01)
(52) U.S. Cl.
USPC ........................................ 514/16.3; 514/21.9
(58) Field of Classification Search
None
See application file for complete search history.

(56) References Cited

U.S. PATENT DOCUMENTS

| | | | |
|---|---|---|---|
| 4,216,209 A | | 8/1980 | Bellini et al. |
| 6,165,746 A | * | 12/2000 | Heitzmann et al. ........... 435/69.1 |
| 6,207,391 B1 | * | 3/2001 | Wu et al. ........................ 435/7.1 |
| 2002/0172692 A1 | * | 11/2002 | Cohen ........................ 424/272.1 |

FOREIGN PATENT DOCUMENTS

| | | |
|---|---|---|
| EP | 1 201 679 A2 | 5/2002 |
| EP | 1 507 795 | 11/2003 |
| JP | 6-277090 A | 10/1994 |
| JP | 6-277091 A | 10/1994 |
| JP | 6-279491 A | 10/1994 |
| JP | 7-101982 A | 4/1995 |
| JP | 2002-121199 A | 4/2002 |
| JP | 2003-511063 A | 3/2003 |
| WO | WO 01/27242 A2 | 4/2001 |
| WO | WO 02/098448 * | 12/2002 |
| WO | WO 03/044044 A1 | 5/2003 |

OTHER PUBLICATIONS

Reid et al (Appl Microbiol Biotechnol "comparison of bovine b-casein hydrolysis by P1 and Piii-type proteinases from *Lactobacullus lactis* subsp. cremoris" (1991) 36:344-351).*
Gauthier et al ('Preparative separation of small molecular weight peptides from casein hydrolysate using gel filtration and immobilized metal ion affinity chromatography' Preparative Biochemistry 20(1) 1990 pp. 23-50).*
Geysen et al ('Use of peptide synthesis to probe viral antigens for epitopes to a resolution of a single amino acid' PNAS v81 Jul. 1984 pp. 3998-4002).*
XP-002410327—Anne Pihlanto-Leppala et al., "Angiotensin I Converting Enzyme Inhibitory Peptides Derived from Bovine Milk Proteins" (1998), Int. Dairy Journal, vol. 8, pp. 325-331.
XP-008065429—Jerry W. Slootstra et al., "Structural aspects of antibody—antigen interaction revealed through small random peptide libraries" (1995), ESCOM Science Publishers B.V., vol. 1, No. 2, pp. 87-96.
F. Minervini, et al., "Angiotensin I-Converting-Enzyme-Inhibitory and Antibacterial Peptides from *Lactobacillus helveticus* PR4 Proteinase-Hydrolyzed Caseins of Milk from Six Species", Applied and Environmental Microbiology, Sep. 2003, pp. 5297-5305, vol. 69, No. 9.
Shoji Kaneko, et al., "Tofu Seizo ni Okeru Koso Riyo ni Kansuru Kenkyu (Dai 3 Ho) Koso Shori ni yoru Kinosei Koka ni tsuite", Research report of Food Technology Research Institute of Nagano Prefecture, Sep. 1, 2003, pp. 53-56, No. 31.
International Search Report for PCT/JP04/018235 dated May 17, 2005.
Supplementary Partial European Search Report issued in counterpart European Patent Application No. 0480161.6 dated Jan. 25, 2007.
European Office Action issued in counterpart European Patent Application No. 04801616.6 dated Nov. 26, 2008.
Japanese Office Action issued on Aug. 3, 2010 in corresponding Japanese Patent Application No. 2005-516450.
The State Intellectual Property Office of the People's Republic of China, Office Action dated Apr. 25, 2012 issued in counterpart Chinese Application No. 201010547460.8.
The State Intellectual Property Office of the People's Republic of China, Office Action dated Aug. 31, 2011 issued in counterpart Chinese Application No. 201010547460.8.
AAN28704, "myoneurin [*Mus musculus*]", GenBank, Sep. 30, 2002.
Hietter, H. et., al. "Isolation and structure of two novel 6-kDa dimeric peptides from the corpora cardiaca of the insect *Locusta migratoria*: Molecular mass determination by mass spectrometry", Eur. J. Biochem. vol. 182, pp. 77-84 (1989).
Office Action issued by the Chinese Patent Office on Oct. 20, 2011 in the corresponding Chinese Patent Application No. 201010547476.9.
Korean Intellectual Property Office, Communication dated Jun. 28, 2012 in a counterpart KR application No. 10-2006-7013202.

* cited by examiner

*Primary Examiner* — Cecilia J Tsang
*Assistant Examiner* — Ronald Niebauer
(74) *Attorney, Agent, or Firm* — Sughrue Mion, PLLC

(57) ABSTRACT

The invention provides a peptide having an activity of inhibiting angiotensin-converting enzyme (ACE), and a food and drink and/or a pharmaceutical composition containing the peptide.

4 Claims, 1 Drawing Sheet

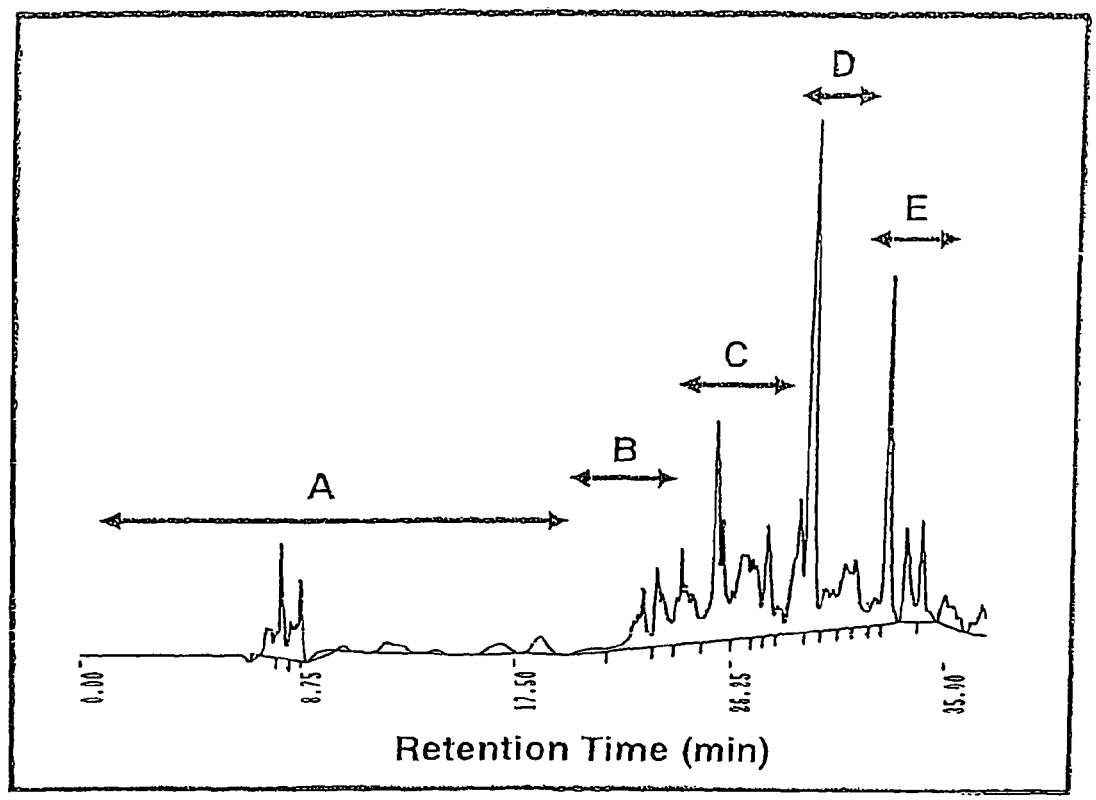

SEQUENCE LISTING

```
<160> NUMBER OF SEQ ID NOS: 7

<210> SEQ ID NO 1
<211> LENGTH: 3
<212> TYPE: PRT
<213> ORGANISM: Artificial Sequence
<220> FEATURE:
<223> OTHER INFORMATION: Synthetic construct

<400> SEQUENCE: 1

Met Ala Pro
1

<210> SEQ ID NO 2
<211> LENGTH: 3
<212> TYPE: PRT
<213> ORGANISM: Artificial Sequence
<220> FEATURE:
<223> OTHER INFORMATION: Synthetic construct

<400> SEQUENCE: 2

Ile His Ala
1

<210> SEQ ID NO 3
<211> LENGTH: 3
<212> TYPE: PRT
<213> ORGANISM: Artificial Sequence
<220> FEATURE:
```

```
<223> OTHER INFORMATION: Synthetic construct

<400> SEQUENCE: 3

Ile Gln Ala
1

<210> SEQ ID NO 4
<211> LENGTH: 4
<212> TYPE: PRT
<213> ORGANISM: Artificial Sequence
<220> FEATURE:
<223> OTHER INFORMATION: Synthetic construct

<400> SEQUENCE: 4

Leu Met Ala Pro
1

<210> SEQ ID NO 5
<211> LENGTH: 4
<212> TYPE: PRT
<213> ORGANISM: Artificial Sequence
<220> FEATURE:
<223> OTHER INFORMATION: Synthetic construct

<400> SEQUENCE: 5

Arg Met Ala Pro
1

<210> SEQ ID NO 6
<211> LENGTH: 4
<212> TYPE: PRT
<213> ORGANISM: Artificial Sequence
<220> FEATURE:
<223> OTHER INFORMATION: Synthetic construct

<400> SEQUENCE: 6

Met Ala Pro Pro
1

<210> SEQ ID NO 7
<211> LENGTH: 5
<212> TYPE: PRT
<213> ORGANISM: Artificial Sequence
<220> FEATURE:
<223> OTHER INFORMATION: Synthetic construct

<400> SEQUENCE: 7

Arg Met Ala Pro Pro
1               5
```

PEPTIDE INHIBITING ANGIOTENSIN CONVERTING ENZYME

TECHNICAL FIELD

The invention relates to a peptide having activity of inhibiting an angiotensin converting enzyme (hereinafter also referred to as ACE). More particularly, the invention relates to a peptide having activity of inhibiting ACE, which is broadly applicable to the suppression of blood pressure increase, as well as to the prevention of hypertension and the like, when it is applied to a pharmaceutical composition as a hypotensive agent, as well as applied as a specified food used for persons having a high blood pressure, nutritious food, functional food, specified health food, hypotensive action-claimable food and drink and the like.

BACKGROUND OF THE INVENTION

ACE is a proteolytic enzyme which plays an important role in the regulation of a blood pressure and amounts of body fluids, and has activity of converting angiotensin I into angiotensin II having strong hypertensive activity, in the rennin-angiotensin system which controls the blood pressure increase. Various studies have been carried out on the inhibitors of this enzyme, and it is known that they have activity of decreasing blood pressure (D. W. Cushman et al., *Biochemical Pharmacology*, Vol. 20, Pages 1637-1648 (1971), Robert J. L. et al., *The Journal of Pharmacology and Experimental Therapeutics*, Vol. 204, Pages 281-288 (1977)). Regarding the ACE inhibitors, various pharmaceutical agents have been studied and are commercially available (Yoshihiro Kaneko et al., "Igaku no Ayumi" (Progress in Medical Science), vol. 122, pages 62-85, 1972; Toshio Hisayoshi et al., "Hitome de Wakaru Koketsuatsu" (Hypertension Recognizable at a Glance), 2nd edition, pages 54-55, 1998; Noboru Toda et al., "Jyunkankei Chiryoyaku no Sayo Mekanizumu" (Action Mechanism of Circulating system Therapeutic Agents), pages 260-265, 1998). In addition, peptides capable of inhibiting ACE have been found from casein and various foods such as gelatin, sardine and bonito. For example, casein-derived peptide VPP (Val-Pro-Pro, $IC_{50}$:9 µM), casein-derived peptide IPP (Ile-Pro-Pro, $IC_{50}$:5 µM) and casein-derived peptide VAP (Val-Ala-Pro, $IC_{50}$:2 µM) and corn protein α-zein-derived LQP (Leu-Gln-Pro, $IC_{50}$: 2 µM) are known (Yasunori Nakamura et al., *Journal of Dairy Science*, Vol. 78, Pages 777-783 (1995); Shinsuke Miyoshi et al., *Agricultural and Biological Chemistry*, Vol. 55 (5), Pages 1313-1318 (1991); Susumu Maruyama et al., *Agricultural and Biological Chemistry*, Vol. 51 (6), Pages 1581-1586 (1987)).

DISCLOSURE OF THE INVENTION

As described above, in view of the present technical situation where studies and developments on ACE inhibitors have been extensively carried out, the present inventors have attempted to develop an ACE inhibitor which is completely novel and has effect.

In order to achieve the aforementioned objects, the inventors conducted examinations from various standpoints, and as a result, synthesized a large number of peptides focusing on peptides, particularly oligopeptides, and then carried out screenings of the thus obtained peptides. As a result, peptides having excellent activity of inhibiting ACE were found, and as a result of the in vitro tests, it was confirmed that these peptides can be used as hypotensive agents, thereby accomplishing the invention.

The invention relates to the following (1) to (9).
(1) A peptide comprising the amino acid sequence represented by SEQ ID NO:1; or
a peptide comprising an amino acid sequence in which one or more amino acids are added to the amino acid sequence represented by SEQ ID NO:1, and having activity of inhibiting angiotensin-converting enzyme.
(2) A peptide comprising the amino acid sequence represented by SEQ ID NO:2; or
a peptide comprising an amino acid sequence in which one or more amino acids are added to the amino acid sequence represented by SEQ ID NO:2, and having activity of inhibiting angiotensin-converting enzyme.
(3) A peptide comprising the amino acid sequence represented by SEQ ID NO:3; or
a peptide comprising an amino acid sequence in which one or more amino acids are added to the amino acid sequence represented by SEQ ID NO:3, and having activity of inhibiting angiotensin-converting enzyme.
(4) An inhibitor for an angiotensin-converting enzyme, which comprises the peptide according to any one of (1) to (3) as an active ingredient.
(5) A food or drink comprising the peptide according to any one of (1) to (3).
(6) A pharmaceutical composition comprising the peptide according to any one of (1) to (3) as an active ingredient.
(7) The pharmaceutical composition according to claim (6), which is an agent for preventing and/or treating diseases caused by abnormality of an angiotensin converting enzyme.
(8) Use of the peptide according to any one of (1) to (3) for the production of an inhibitor for an angiotensin-converting enzyme.
(9) Use of the peptide according to any one of (1) to (3) for the production of an agent for preventing and/or treating diseases caused by abnormality of an angiotensin converting enzyme.

BRIEF DESCRIPTION OF THE DRAWING

FIG. 1 shows an HPLC chromatogram of cheese-derived peptides.

BEST MODE FOR CARRYING OUT THE INVENTION

Specific examples of the peptide of the invention include the following peptides of (a) to (f).
(a) A peptide comprising the amino acid sequence represented by SEQ ID NO:1;
(b) a peptide comprising the amino acid sequence represented by SEQ ID NO:2;
(c) a peptide comprising the amino acid sequence represented by SEQ ID NO:3;
(d) a peptide comprising an amino acid sequence in which one or more amino acids are added to the amino acid sequence represented by SEQ ID NO:1, and also having activity of inhibiting ACE;
(e) a peptide comprising an amino acid sequence in which one or more amino acids are added to the amino acid sequence represented by SEQ ID NO:2, and also having activity of inhibiting ACE; and
(f) a peptide comprising an amino acid sequence in which one or more amino acids are added to the amino acid sequence represented by SEQ ID NO:3, and also having activity of inhibiting ACE.

In the followings, the peptide comprising the amino acid sequence represented by SEQ ID NO:1 (Met-Ala-Pro), the peptide comprising the amino acid sequence represented by SEQ ID NO:2 (Ile-His-Ala) and the peptide comprising the amino acid sequence represented by SEQ ID NO:3 (Ile-Gln-Ala) are also referred to as MAP, IHA and IQA, respectively.

Regarding the peptides comprising an amino acid sequence in which one or more amino acids are added to the amino acid sequence represented by SEQ ID NOs:1 to 3 and also having activity of inhibiting ACE, the amino acids to be added are not particularly limited, and optional amino acids can be used so long as the peptides have the activity of inhibiting ACE. The number of the amino acids to be added is not particularly limited, and optional numbers of amino acids can be used so long as the peptides have the activity of inhibiting ACE. However, in general, the number of the amino acids to be added is from 1 to 10, preferably from 1 to 5, more preferably from 1 to 3, still more preferably 1 or 2, and particularly preferably 1.

Specific examples include a peptide comprising the amino acid sequence represented by SEQ ID NO:4 (Leu-Met-Ala-Pro), a peptide comprising the amino acid sequence represented by SEQ ID NO:5 (Arg-Met-Ala-Pro), a peptide comprising the amino acid sequence represented by SEQ ID NO:6 (Met-Ala-Pro-Pro), a peptide comprising the amino acid sequence represented by SEQ ID NO:7 (Arg-Met-Ala-Pro-Pro) and the like.

The peptides of the invention may be those to which an industrially used salt such as chloride, acetate, sulfate, succinate or tartarate is added, but it is preferable that a food-applicable or pharmaceutically acceptable salt is added.

The peptides of the invention can be used alone or as a mixture of two or more peptides.

The peptides of the invention may be produced by conventional peptide-synthesis methods, or they may be prepared by enzymatically or chemically hydrolysis of a milk protein such as casein. Also, microbial fermentation may be employed.

The inhibitor for ACE of the invention contains the peptide of the invention, and can be used in various forms such as food and drink, specified health food, nutritious and functional food, specified use food, healthy food, quasi-drug, pharmaceutical composition and the like. For example, it may be directly administered as a pharmaceutical composition or a quasi-drug, or directly taken as a specified use food such as healthy food and specified health food; or nutritious and functional food, or taken by adding it in advance to various foods such as milk, soft drink, fermented milk, yoghurt, cheese, bread, biscuit, cracker and pizza crust.

For the purpose of producing the aforementioned foods, water, protein, saccharides, lipids, vitamins, minerals, organic acids, fruit juice, flavors and the like can be combined as the main components. Examples include animal and plant proteins such as whole milk powder, skim milk powder, partially skimmed milk powder, whey powder, whey protein, concentrated whey protein, isolated whey protein, α-casein, β-casein, κ-casein, β-lactoglobulin, α-lactoalbumin, lactoferrin, soybean protein, egg protein, meat protein and hydrolysates thereof; various milk-derived components such as butter, milk serum mineral, cream, whey, milk serum mineral, non-protein nitrogen, sialic acid, phospholipid and lactose; carbohydrates such as sucrose, glucose, fructose, sugar alcohols, maltose, oligosaccharides, modified starch (dextrin, as well as soluble starch, British starch, oxidized starch, starch ester, starch ether etc.) and dietary fiber; animal oils and fats such as lard and fish oil; plant oils such as palm oil, safflower oil, corn oil, rapeseed oil, coconut oil and fractional oil thereof including hydrogenated oil, ester interchange oil and the like; various vitamins such as vitamin A, vitamin B group, vitamin C, vitamin D group, vitamin E, vitamin K group, vitamin P, vitamin Q, niacin nicotinic acid, pantothenic acid, biotin, inositol, choline, folic acid; minerals such as calcium, potassium, magnesium, sodium, chlorine, copper, iron, manganese, zinc, selenium, fluorine, silicon, iodine; and organic acids and organic acid salts such as malic acid, citric acid, lactic acid, tartaric acid and the like, and one or two or more kinds thereof can be optionally selected and added. In addition to synthesized products, if necessary, it is also preferable to add them as a food containing them in a large amount.

When the products of the invention are used as pharmaceutical compositions or quasi-drugs, they can be administered as various salts. For example, administration thereof as a salt with hydrochloric acid, acetic acid, formic acid or the like can be mentioned. Methods of administration include oral administration, percutaneous administration, intestinal administration, vascular administration, intravenous injection, intramuscular injection, nasal dropping, ophthalmic dropping, inhalation, rectal administration and the like. In addition, they can be administered in various forms. For example, administrations in the form of tablets, troches, capsules, granules, powders, syrups, suspensions, solutions and the like can be mentioned. These various pharmaceutical preparations can be prepared, in accordance with usual methods, by using conventional auxiliary agents generally used in the technical field of producing pharmaceutical preparations such as a filler, a binder, a disintegrating agent, a lubricant, a corrective, a solubilizing agent, a suspending agent and a coating agent with the principal agent.

Since the peptides of the invention have the activity of inhibiting ACE, they can be used in the prevention and/or treatment of diseases relating to ACE in the rennin-angiotensin system, the quinine-kallikrein system and the like. Diseases relating to ACE include hypertension, arteriosclerosis, vascular hypertrophy, myocardial infarction, heart failure, cardiac hypertrophy, renal insufficiency, diabetes mellitus and the like.

The active ingredient according to the invention shows excellent safety, because its toxicity is absolutely absent or extremely small, and when it was orally administered to mice at a dose of 500 mg per day, completely no acute toxicity was found. Accordingly, when it is used in the form of food or drink, the amount of the active ingredient to be used has no particular limitation in every case of its use for prevention, health and food and drink, and when it is used as a pharmaceutical, it may be optionally used within the aforementioned range depending on each patient. For example, in the case of oral ingestion, the amount thereof to be used varies depending on the symptom, age, body weight, administration method, dosage form and the like, but in general, it can be administered approximately in an amount of from 0.1 mg to 1,500 mg per adult once a day or dividing the daily dose into several doses. In addition, since the active ingredient does not show particular acute toxicity even when it is taken in a large amount, it may be optionally used in a large amount exceeding the above range.

The followings describe the production method of the peptides of the invention, by referring to MAP as its example. IHA, IQA and other peptides containing these peptides as partial peptides can also be produced in the same manner.

1. Preparation Method of MAP

MAP can be preferably prepared by the following method.

In the following preparation method, a combination of a substrate containing MAP as its partial structure and an enzyme capable of cutting out MAP from the substrate is used. As the substrate, β-casein is preferably used, but it may also be an animal or plant protein such as milk, milk-derived component, whole milk powder, skim milk powder, partially skimmed milk powder, casein, soybean protein, egg protein, meat protein, beans or wheat or a hydrolysate thereof. β-Casein is rich in proline, and about 17% of its sequence is proline. In addition, since β-casein is contained in an amount of 33.6% in milk casein micelle, it can be prepared therefrom in a large amount.

The substrate is dissolved in water with a concentration of from 0.1 to 70% by weight, preferably from 0.1 to 60% by weight, further preferably from 0.3 to 50% by weight. Protease N "Amano" G (manufactured by Amano Enzyme Inc.) is added thereto in an amount of from 0.1 to 10% by weight, preferably from 0.3 to 2% by weight, based on the substrate protein content, and then the pH thereof is adjusted to from 4.5 to 6.0, preferably from 4.5 to 5.0, using organic acid or inorganic acid such as citric acid solution, lactic acid or hydrochloric acid, followed by stirring at from 15 to 50° C., preferably from 20 to 40° C., more preferably from 30 to 40° C. for thereby causing the degradation. After the degradation for 40 to 50 hours, each of Umamizyme G (manufactured by Amano Enzyme Inc.) and Flavourzyme (manufactured by Novozymes Corporation) is added thereto in an amount of from 0.01 to 10% by weight, preferably from 0.1 to 5% by weight, based on the substrate protein content, and then the pH thereof is adjusted to from 3.5 to 5.0, preferably from 3.5 to 4.0. The degradation is further carried out for 5 to 10 days under stirring at from 15 to 50° C., preferably from 20 to 40° C., more preferably from 30 to 40° C. The enzymes are deactivated by a heating treatment at from 50 to 110° C., preferably from 60 to 100° C., more preferably from 80 to 100° C., for 10 to 20 minutes, and then the pH thereof is adjusted to from 4.5 to 6.0, preferably from 4.5 to 5.0.

2. Method for Confirming Formation of MAP

Regarding the method for confirming the formation of MAP, each of water-soluble fraction of an enzyme digestion sample and an MAP standard sample is analyzed by LC-MS, and the formation of MAP is judged by the presence or absence of the peaks at the same retention time of MAP of the MAP standard sample. The enzyme digestion samples prepared in the above 1. are centrifuged at 4° C. and at 10,000 g for 40 minutes, and the water-soluble fraction is recovered and further freeze-dried. Each of the freeze-dried samples is again dissolved in the following mobile phase with a concentration of 100 μg/ml, and a 5 μl portion thereof is injected. The MAP standard sample is dissolved in the following mobile phase with a concentration of 5 μg/ml, and a 5 μl portion thereof is injected. When the MAP standard sample is analyzed under the following analytical conditions, the peak of MAP is observed at a retention time of about 17 minutes. By analyzing the water-soluble fractions of the enzyme digestion samples under the same analytical conditions, samples from which the peak is observed at about 17 minutes are judged as "MAP-positive", and samples from which the peak is not observed are judged as "MAP-negative".

Column: CAPCEL PAK C18 MG (φ 2.0×250 mm, manufactured by SHISEIDO CO., LTD.)
Mobile phase: 4% acetonitrile solution containing 0.05% formic acid
Flow rate: 0.17 ml/min
Column temperature: 40° C.
Detector: ESI positive
Molecular weight: 318

The invention is further described below in detail with reference to examples, but the invention is not limited thereto.

Example 1

A 100 g portion of Denmark Skim cheese (crushed with a meat chopper) was mixed with 50 g of sterile water, and then 18 g of starter bacteria (3 kinds including *Lactococcus lactis* subsp. *lactis, Lactococcus cremoris* and *Lactococcus diacetylactis*) and 0.34 g of sodium chloride were added, followed by stirring. Subsequently, 0.6 g of Protease N "Amano" G (manufactured by Amano Enzyme Inc.) was added thereto, and the mixture was shaken at 34° C. to thereby carry out degradation. Forty-eight hours thereafter, the PH thereof was adjusted to 4.1 with citric acid, and 0.3 g for each of Umamizyme G (manufactured by Amano Enzyme Inc.) and Flavourzyme (manufactured by Novozymes Corporation) were added thereto, followed by shaking at 34° C. to thereby carry out degradation. Six days thereafter, the pH thereof was adjusted to 7.0 and sterile water was subsequently added to make the whole amount of 200 g. The enzymes were deactivated by heating at 110° C. for 15 minutes. The insoluble matters were removed by centrifugation, and then peptides were purified out by HPLC. Using YMC-Pack R & D ODS column (manufactured by YMC Corporation, 20×250 mm), elution was carried out by a linear gradient (50 min) of from 0.1% aqueous trifluoroacetic acid solution to 70% aqueous acetonitrile solution containing 0.1% trifluoroacetic acid (flow rate: 7.5 ml/min, detection: 214 nm, column temperature: 40° C.). An HPLC chromatogram is shown in FIG. 1. The fraction D eluted at from 27 to 31 minutes was fractionated, and then purified by the same column chromatography, to thereby isolate tripeptides having sequences of Met-Ala-Pro, Ile-His-Ala and Ile-Gln-Ala.

Example 2

Each of the peptides of SEQ ID NOs:1 to 7 was synthesized using an automatic peptide synthesizer. It was confirmed by reverse phase HPLC that the purity of each of the thus obtained peptides is 95%. Each of these synthetic peptides was dissolved in 0.1 M borate buffer (pH 8.3). Subsequently, 0.1 ml of an enzyme solution (Angiotensin Converting Enzyme: 2 units/ml) and 0.04 ml of each of the sample solutions were mixed therewith, followed by heating to 37° C. A 0.1 ml portion of a substrate solution (Hippuryl-His-Leu; N-Benzoyl-Gly-His-Leu) was added thereto, followed by thorough stirring. After allowing the mixture to react at 37° C. for 60 minutes, the reaction was stopped by adding 0.13 ml of 1 N hydrochloric acid. Then, 0.85 ml of ethyl acetate was added thereto, followed by shaking for 1 minute, and then the mixture was centrifuged at 3,000 rpm for 10 minutes. A 0.7 ml portion of the supernatant was recovered, and the solvent was removed using a centrifugal evaporator (about 30 minutes). The residual matters were dissolved by adding 0.5 ml of distilled water, and the absorbance at a wavelength of 228 nm was measured.

The activity of inhibiting ACE (%) was calculated by the following mathematical expression 1.

$$\text{Activity of inhibiting ACE}(\%) = \{(A-B)-(C-D)\}/(A-B) \times 100 \quad \text{Mathematical expression 1}$$

In this connection, A in the expression is absorbance of the control when the enzyme is used, B is the absorbance of the control when the enzyme is not used, C is absorbance of the sample when the enzyme is used, and D is absorbance of the sample when the enzyme is not used. In addition, 0.1 M borate buffer was used in the control instead of the sample solution.

Based on the thus obtained ACE inhibitory activities, $IC_{50}$ of each peptide was calculated. The results are shown in the following table.

TABLE 1

| | $IC_{50}$ |
|---|---|
| Met-Ala-Pro | 0.8 μM |
| Ile-His-Ala | 394.3 μM |
| Ile-Gln-Ala | 64.1 μM |

As is clear from the above results, it was confirmed that each of the three kinds of the peptides exerts high activity of inhibiting ACE. Among all, the peptide MAP (Met-Ala-Pro) exerts particularly high inhibitory activity.

Example 3

ACE inhibitory activities (%) of the 4 peptides, Leu-Met-Ala-Pro (SEQ ID NO:4), Arg-Met-Ala-Pro (SEQ ID NO:5), Met-Ala-Pro-Pro (SEQ ID NO:6) and Arg-Met-Ala-Pro-Pro (SEQ ID NO:7), which have Met-Ala-Pro as a partial structure, were obtained by the same method of Example 2, and their $IC_{50}$'s were calculated.

The results are shown in Table 2.

TABLE 2

| | | $IC_{50}$ |
|---|---|---|
| Leu-Met-Ala-Pro | (SEQ ID NO: 4) | 27.9 μM |
| Arg-Met-Ala-Pro | (SEQ ID NO: 5) | 24.0 μM |
| Met-Ala-Pro-Pro | (SEQ ID NO: 6) | 28.3 μM |
| Arg-Met-Ala-Pro-Pro | (SEQ ID NO: 7) | 254.9 μM |

From the above results, it was found that each of the peptides having the peptide MAP as a partial structure exerts high activity of inhibiting ACE.

While the invention has been described in detail and with reference to specific embodiments thereof, it will be apparent to one skilled in the art that various changes and modifications can be made therein without departing from the spirit and the scope thereof.

This application is based on Japanese patent application No. 2003-401405 filed Dec. 1, 2003, the entire contents thereof being hereby incorporated by reference.

INDUSTRIAL APPLICABILITY

Since the peptides of the invention have markedly high activity of inhibiting ACE, they can exert the effect to suppress the increase of blood pressure at a small dose, so that they are not only useful as preventive or therapeutic agents for suppressing the blood pressure increase but also used as preventive or therapeutic foods and drinks for use in the suppression of the blood pressure increase, which do not show unpleasant tastes such as strong bitterness.

SEQUENCE LISTING FREE TEXT

SEQ ID NO:1—Explanation of artificial sequence: synthetic peptide
SEQ ID NO:2—Explanation of artificial sequence: synthetic peptide
SEQ ID NO:3—Explanation of artificial sequence: synthetic peptide
SEQ ID NO:4—Explanation of artificial sequence: synthetic peptide
SEQ ID NO:5—Explanation of artificial sequence: synthetic peptide
SEQ ID NO:6—Explanation of artificial sequence: synthetic peptide
SEQ ID NO:7—Explanation of artificial sequence: synthetic peptide

The invention claimed is:

1. An isolated peptide selected from the group consisting of
   (a) a peptide consisting of the amino acid sequence represented by SEQ ID NO:3;
   (b) a peptide consisting of the amino acid sequence represented by SEQ ID NO:4; and
   (c) a peptide consisting of the amino acid sequence represented by SEQ ID NO:5.

2. An inhibitor for an angiotensin-converting enzyme, which comprises the peptide according to claim 1 as an active ingredient in an amount effective to inhibit angiotensin-converting enzyme.

3. A preparation comprising the peptide according to claim 1 and a food or drink.

4. A pharmaceutical composition comprising the peptide according to claim 1 as an active ingredient and a pharmaceutically acceptable excipient.

* * * * *